United States Patent [19]
Schläpfer

[11] Patent Number: 6,063,090
[45] Date of Patent: May 16, 2000

[54] DEVICE FOR CONNECTING A LONGITUDINAL SUPPORT TO A PEDICLE SCREW

[75] Inventor: Fridolin Schläpfer, Glarus, Switzerland

[73] Assignee: Synthes (U.S.A.), Paoli, Pa.

[21] Appl. No.: 09/319,732

[22] PCT Filed: Dec. 12, 1996

[86] PCT No.: PCT/CH96/00437

§ 371 Date: Jun. 11, 1999

§ 102(e) Date: Jun. 11, 1999

[87] PCT Pub. No.: WO98/25534

PCT Pub. Date: Jun. 18, 1998

[51] Int. Cl.$^7$ ............................................. A61B 17/56
[52] U.S. Cl. ............................................. 606/61; 606/73
[58] Field of Search .................. 606/60, 61, 69, 606/70, 71, 72, 73, 54, 59, 65, 66, 104; 623/16, 17

[56] References Cited

U.S. PATENT DOCUMENTS

| | | | |
|---|---|---|---|
| 4,946,458 | 8/1990 | Harms et al. | 606/61 |
| 5,207,678 | 5/1993 | Harms et al. | 606/61 |
| 5,261,909 | 11/1993 | Sutterlin et al. | 606/61 |
| 5,352,226 | 10/1994 | Lin | 606/61 |
| 5,466,237 | 11/1995 | Byrd, III et al. | 606/61 |
| 5,474,551 | 12/1995 | Finn et al. | 606/61 |
| 5,474,555 | 12/1995 | Puno et al. | 606/73 |
| 5,499,983 | 3/1996 | Hughes | 606/61 |
| 5,501,684 | 3/1996 | Schlapfer et al. | 606/73 |
| 5,520,690 | 5/1996 | Errico et al. | 606/61 |
| 5,527,314 | 6/1996 | Brumfield et al. | 606/61 |
| 5,531,746 | 7/1996 | Errico et al. | 606/61 |
| 5,549,608 | 8/1996 | Errico et al. | 606/61 |
| 5,554,157 | 9/1996 | Errico et al. | 606/61 |
| 5,575,791 | 11/1996 | Lin | 606/61 |
| 5,575,792 | 11/1996 | Errico et al. | 606/61 |
| 5,578,033 | 11/1996 | Errico et al. | 606/61 |
| 5,584,834 | 12/1996 | Errico et al. | 606/61 |
| 5,586,984 | 12/1996 | Errico et al. | 606/61 |
| 5,591,166 | 1/1997 | Bernhardt et al. | 606/61 |
| 5,607,426 | 3/1997 | Ralph et al. | 606/61 |
| 5,609,593 | 3/1997 | Errico et al. | 606/61 |
| 5,609,594 | 3/1997 | Errico et al. | 606/61 |
| 5,647,873 | 7/1997 | Errico et al. | 606/61 |
| 5,669,911 | 9/1997 | Errico et al. | 606/61 |
| 5,672,176 | 9/1997 | Biedermann et al. | 606/61 |
| 5,683,392 | 11/1997 | Richelsoph et al. | 606/61 |
| 5,688,273 | 11/1997 | Errico et al. | 606/61 |
| 5,690,630 | 11/1997 | Errico et al. | 606/61 |
| 5,728,098 | 3/1998 | Sherman et al. | 606/61 |
| 5,733,285 | 3/1998 | Errico et al. | 606/61 |
| 5,735,853 | 4/1998 | Olerud | 606/71 |
| 5,741,255 | 4/1998 | Krag et al. | 606/61 |
| 5,752,957 | 5/1998 | Ralph et al. | 606/61 |
| 5,782,831 | 7/1998 | Sherman et al. | 606/61 |
| 5,797,911 | 8/1998 | Sherman et al. | 606/61 |
| 5,810,819 | 9/1998 | Errico et al. | 606/61 |
| 5,817,094 | 10/1998 | Errico et al. | 606/61 |
| 5,863,293 | 1/1999 | Richelsoph | 606/61 |
| 5,879,350 | 3/1999 | Sherman et al. | 606/61 |

FOREIGN PATENT DOCUMENTS

| | | |
|---|---|---|
| 0 330 881 A1 | 9/1989 | European Pat. Off. |
| 195 09 332 C1 | 8/1996 | Germany. |
| WO 94/00066 | 1/1994 | WIPO. |
| WO 98/34554 | 8/1998 | WIPO. |

*Primary Examiner*—Gene Mancene
*Assistant Examiner*—Pedro Philogene
*Attorney, Agent, or Firm*—Pennie & Edmonds LLP

[57] ABSTRACT

The invention relates to a device used to connect a longitudinal support to a pedicle screw by an accommodating head having a channel to accommodate the longitudinal support, wherein it is possible to freely choose from or mix laterally open, top open or closed accommodating heads. A top open accommodating head facilitates, for example, insertion of the longitudinal support, whereas a lateral opening enables lateral corrections. The pedicle screw and the accommodating head are connected via a conical collet chuck in the accommodating head and by a spherical head on the pedicle screw. The present invention allows engagement of the pedicle screw in the accommodating head after the pedicle screw has been inserted into bone.

20 Claims, 3 Drawing Sheets

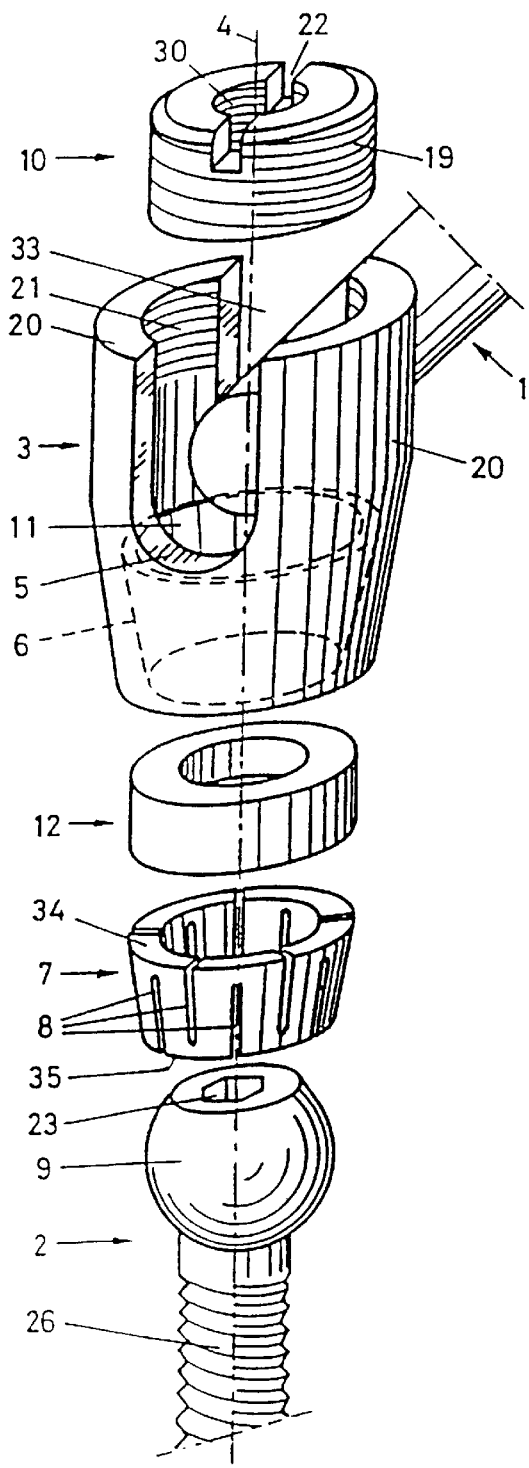
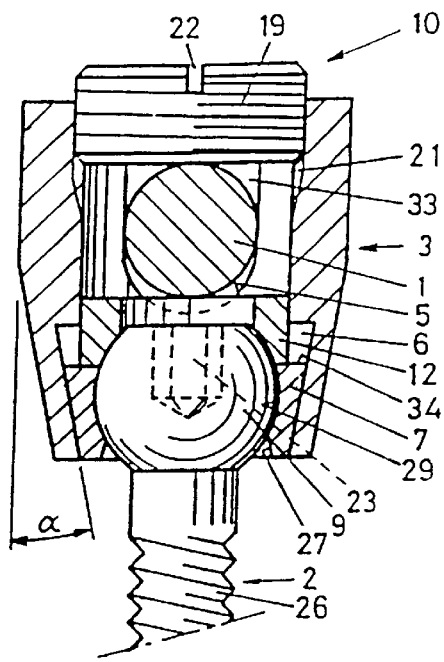
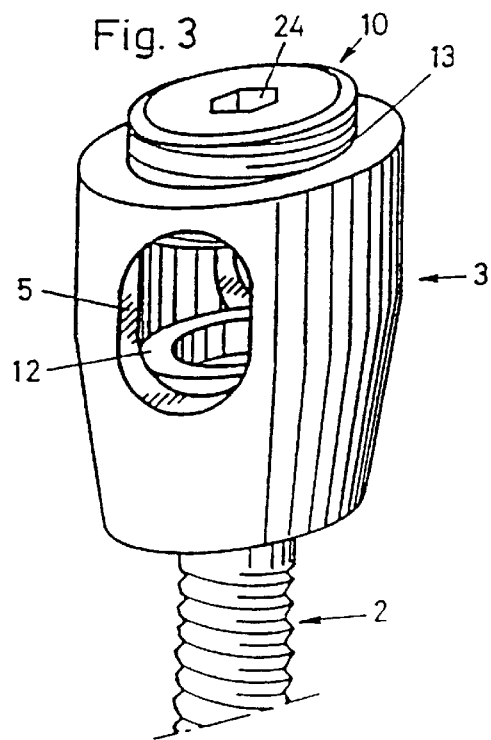

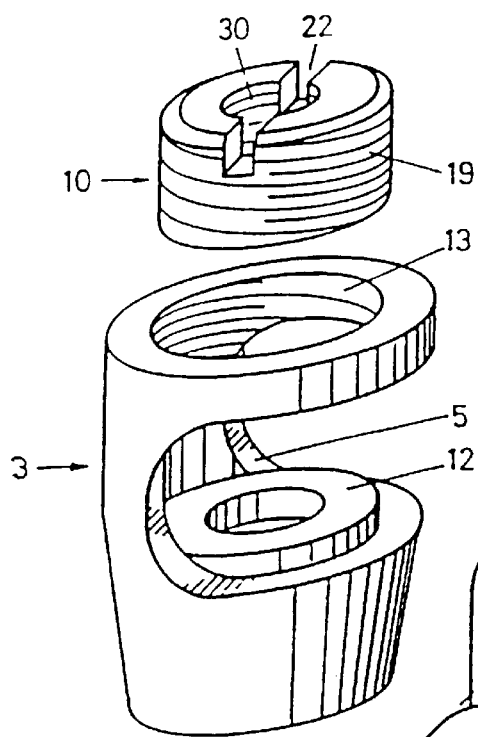
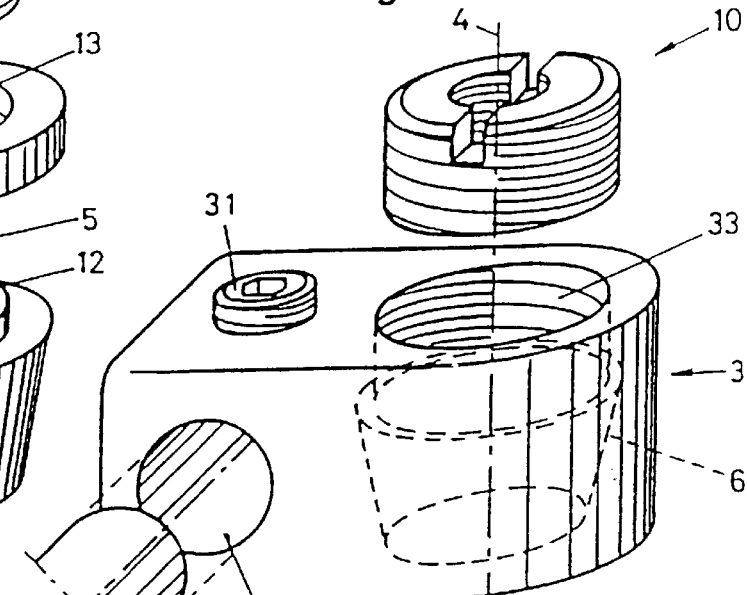
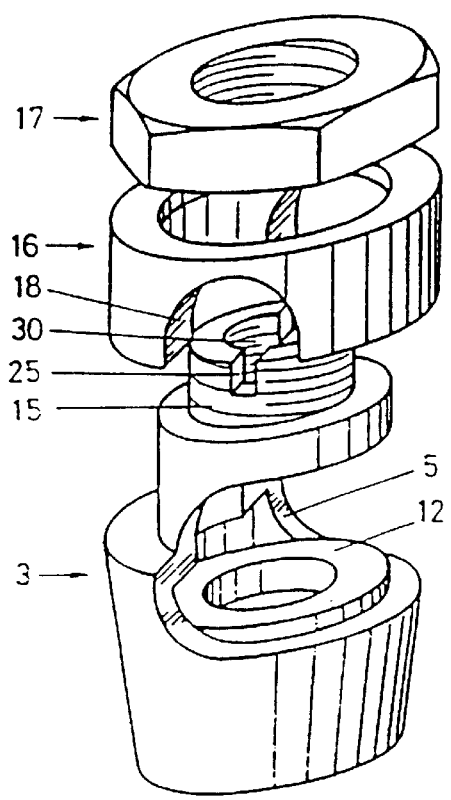
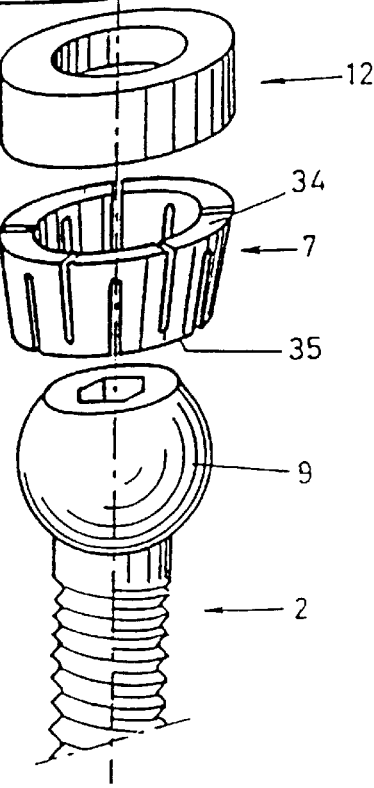

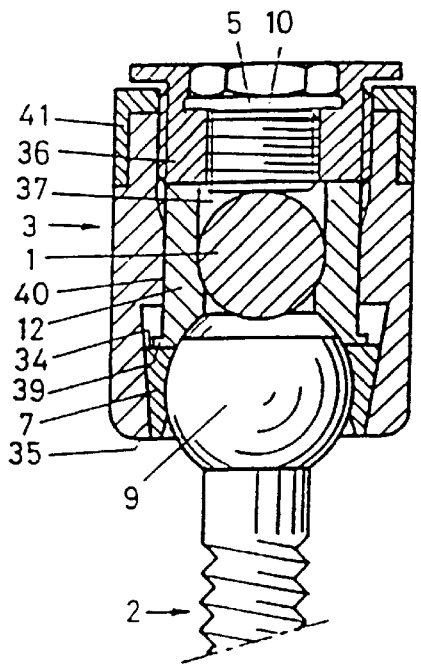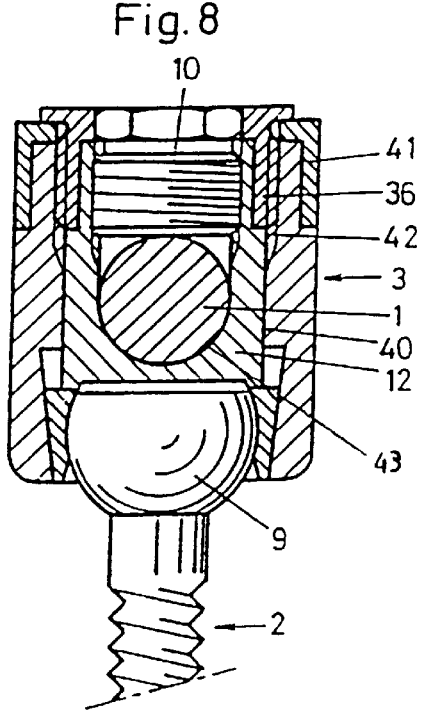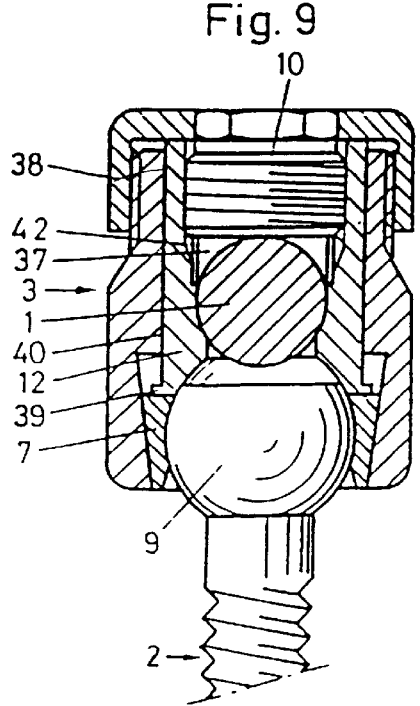

DEVICE FOR CONNECTING A LONGITUDINAL SUPPORT TO A PEDICLE SCREW

FIELD OF THE INVENTION

The invention relates to a spinal fixation system, and in particular to a device for connecting a longitudinal support to a pedicle screw.

BACKGROUND

There are already known several pedicle screws for the fixation of the vertebral column having the advantage that the different pedicle screws can be implanted independently from the longitudinal support. The longitudinal support is subsequently entered into the pedicle screw either sidewardly or from the top and fastened. For example, such a pedicle screw is disclosed in EP-B 0 330 881 SHERMAN.

The disadvantage of these known pedicle screws consists in the relatively complicated locking mechanism to fasten the longitudinal support after inserting it into the openly shaped head of the pedicle screw. Furthermore, in most cases the head of the screw is only adjustable with respect to the position of the longitudinal support to a limited degree, thereby requiring complicated and time-consuming adjustment of the longitudinal support.

DE-C 195 09 332 discloses an anchoring element in which the spherical head of a pedicle screw can be locked into a compressible pressure element at various angles. A tensioning of the pressure element in the retainer head is generated due to a mechanism previously disclosed in PCT/CH92/00125, i.e., by moving the truncated cone shaped pressure element in a complementorily conically shaped bore until the pressure element jams in the bore hole. By jamming the pressure element, the spherical head of the bone screw can be secured at various angles.

The disadvantages of these known devices include the following:

a) The design of the hollow cylindrical pressure element which accepts the spherical head provides only two downwardly open longitudinal slots extending in the same direction (in the direction of the bone screw). Therefore, while jamming no homogenous encompassment of the spherical head of the bone screw via the lamellas of the slotted pressure element takes place. This inhomogenous encompassment of the spherical head causes a reduced jam force;

b) The bone screw must be mounted by inserting it together with the pressure element from the top via the recess for the tensioning element and fastened secured against rotation in the device. This means the bone screw cannot be screwed in independently from the retainer head. The retainer head enables no mounting after the implantation of the bone screw. As a result a reduced view while screwing in the bone screw with mounted retainer head is yielded. If a system with differently formed retainer heads should be offered, the system consists, because of the premounting of the bone screw caused by the design, of n*m implants [where n=number of head variants and m=number of lengths of the screws] instead of n+m implants. A further disadvantage is that a change of the retainer heads in situ caused by the situation is impossible.

c) The low stability of the angle, which permits only a fixation by tension boom;

d) Through the tension means, the longitudinal support of the device and the spherical head of the bone screw are fastened at the same time. A loosening of the tension means causes a failure of the whole fixation system at once; and e) Depending on the situation, one would like to fasten the connection between the device and the spherical head of the bone screw independently from the longitudinal support to distract or compress between longitudinal support and bone screw via the longitudinal support without loss of angle.

SUMMARY OF THE INVENTION

The aim of the invention is to provide a device for the connection of a longitudinal support with a pedicle screw with the following properties:

easy handling inserting of screw part of the device without the retainer head;

possibility of subsequent onclicking of the retainer head;

depending on the situation or the preference of the surgeon free choice of or mixture of sidewardly open, upwardly open or closed retainer heads. For example an upwardly open retainer head eases the insert of the longitudinal support while a sideward opening enables correction sidewardly; and depending on the embodiment separate fastening of the longitudinal support and spherical head of the bone screw.

The invention solves the posed aims with a spinal fixation system comprising a longitudinal member positionable along a spinal column, a fastener having a threaded end for engaging a vertebra, and a connector member for connecting the fastener and the longitudinal member. The connector member includes a channel extending through its side surfaces for receiving the longitudinal member, a tapered opening extending through its bottom surface for receiving the fastener, a top opening extending through its top surface and operatively associated with the tapered opening, a fastener clamping element, and a tension element insertable in the top opening. The fastener clamping element has a hollow truncated cone shape and a plurality of slots for securing the fastener in the tapered opening at a surgeon selected angle relative to the connector member and longitudinal member. Insertion of the tension element in the top opening causes downward movement of the fastener clamping element in the tapered opening and thereby radial compression of the fastener clamping element to secure the fastener at the surgeon selected angle.

In one embodiment, the device according to the invention consists of a retainer head accepting the longitudinal support where a pedicle screw with a preferably spherical head can be subsequently clicked in and fastened. By screwing in the tension means in the fixation device, the longitudinal support is fixed (both axially and rotationally) in the device, and, at the same time, the pedicle screw is fastened at the desired angle. The locking screw used as a tension means simultaneously presses on the longitudinal support inserted into the device and the hollow truncated cone into which the head of the pedicle screw is inserted. For optimal load transmission from the longitudinal support to the hollow truncated cone, a rigid insert is advantageously inserted between the longitudinal support and the hollow truncated cone. Depending on the design of the insert and the tension means, the present invention also enables separate fastening of the longitudinal support and the head of the bone screw.

Thus, the device according to the invention offers the advantage compared to the known devices that the pedicle screws are not only fastenable perpendicular to the longitudinal support but also at an angle of up to ±25° with respect to the longitudinal support. Furthermore, because of the distance between the center of rotation at the retainer head and the axis of the longitudinal support, sideward deviations between the longitudinal support and the pedicle screw may be compensated for. Although the amount of compensation will depend on the thickness of the longitudinal support, compensation between 4 and 10 mm is possible. This compensation is particularly important if the longitudinal support was inaccurately bent. Another advantage of the device according to the invention is, that, depending on the embodiment of the rigid insert and the tension means, the longitudinal support and the head of the bone screw may be separately fastened.

The head of the pedicle screw is provided preferably with transverse grooves or transverse fins to reach a better fastening (jamming against the spring chuck).

The stability of the angle between the screw and longitudinal support may be improved by making the head of the screw of a relatively hard material (e.g. Ti—Al—Nb alloy) and the hollow truncated cone of a relatively soft material (e.g. commercially pure titanium).

The stability of the angle can also be increased by roughening the head of the pedicle screw and/or the complementary cavity in hollow truncated cone with a three dimensional structure e.g. in the form of grooves. Thus, the structure of relatively hard material situated at the head of the screw is pressed into the relatively unrigid material of the hollow truncated cone.

To screw in the pedicle screws into the bone they are preferably provided in the spherical head with a hexagon socket. If the head is through cannulated only, the pedicle screw or the entire device may be screwed together. The latter especially has the advantage that at any time the device may be screwed in further or screwed back to gain a leveling of the device.

The screw head or click mechanism of the current invention has the further advantage compared to other known click mechanisms, e.g. according to U.S. Pat. No. 5,549,608, in that after succeeded onclicking, an erroneous loosening of the established connection is not possible through the manipulations to be performed. Should the established connection be loosened again intentionally, then this requires the use of a particular instrument.

BRIEF DESCRIPTION OF THE FIGURES

The invention and further embodiments of the invention are further discussed in the following with the help of different embodiments, wherein:

FIG. 1 is a perspective exploded view of the device according to the invention with an upwardly open retainer head together with a longitudinal support, a pedicle screw with spherical head and a tension means;

FIG. 2 is a longitudinal cut through the device according to the invention according to FIG. 1 along the central axis;

FIG. 3 is a perspective view of a modified device according to the invention with a closed channel for the acceptance of a longitudinal support as well as a tension means;

FIG. 4 is a perspective view of a modified device according to the invention with a sidewardly (instead of upwardly) open channel for the acceptance of a longitudinal support as well as a tension means;

FIG. 5 is a perspective view of a modified device according to the invention with a sidewardly open channel for the acceptance of a longitudinal support as well as a supplementary sleeve and nut to the fastening of the longitudinal support;

FIG. 6 is a perspective view of a modified device according to the invention where the longitudinal support is distant to the central axis;

FIG. 7 is a longitudinal cut through a modified device according to the invention where the longitudinal support and the preferably spherical head of the bone screw may be fastened separately;

FIG. 8 is a longitudinal cut through a modified device according to the invention with features as disclosed in FIG. 7 with the difference that the locking screws for the fastening of the longitudinal support and the preferably spherical head of the bone screw are mechanically decoupled; and FIG. 9 is a longitudinal cut through a modified device according to the invention according to FIG. 8 with the advantage that the longitudinal support is insertable from above.

DETAILED DESCRIPTION OF THE PREFERRED EMBODIMENTS

The device according to the invention represented in FIGS. 1 and 2 essentially consists of a retainer head 3 with the central axis 4 and upwardly open channel 5 shaped as a yoke and running transversely to the central axis 4 as well as a downwardly open cavity 6 shaped as a truncated cone tapering downwardly with the central axis 4 wherein spring chuck 7 shaped as a hollow truncated cone with alternating slots is provided coaxially removable which is formed to the acceptance of the head 9 of a pedicle screw 2.

As shown in FIG. 2, the cavity 6 shaped as a truncated cone practically provides a half cone angle $\alpha/2$ of about 6°. The spring chuck 7 shaped as a hollow truncated cone having alternating slots 8 provides a corresponding half cone angle $\alpha/2$ of about 6°. The spring chuck 7 can, by means of its slots 8, be extended in its diameter by about 0.4 mm and be compressed by up to 1 mm so that the head 9 of the pedicle screw 2 is snappable into it. For this purpose the interior of the spring chuck 7 is shaped concave, preferably in the form of a hollow sphere.

The cavity 6 extends upwardly in the axial direction into the channel 5 so that the spring chuck 7, and the above lying insert 12, which is preferably formed as a hollow cylindrical member (e.g. in the shape of a washer), is pressable axially downwards via the longitudinal support 1 inserted in the channel 5—when the longitudinal support 1 is axially and rotationally fixed in the channel 5 by means of the tension means 10. At the same time as the downward axial displacement of the spring chuck 7 inside the cavity 6, which tapers conically downwards and is preferably shaped as a truncated cone, a spring chuck 7 compresses radially inward so that the head 9 of the pedicle screw 2, which was previously snapped into the spring chuck 7 from below, is jammed and fastened in its relative position to the retainer head 3 (and thus with the longitudinal support 1). The decoupling between the spring chuck 7 and the insert 12 provides a homogenous encapsulation of the head 9 to result in an optimal firmness of the connection between retainer head 3 and the pedicle screw 2.

The tension means 10 has an external thread 19 and the channel 5 has, in the region of the two legs 20 forming a yoke, a corresponding internal thread 21. To screw the external thread 19 into the internal thread 21, the tension means 10 has a transverse slot 22 at its open end and an internal thread 30 to accept an correspondingly shaped manipulating instrument (not shown in the drawings). Instead of the transverse slot 22 and the internal thread 30 a hexagonal socket for instance can also be used.

The function of the insert 12 consists in special case just therein to enable a transmission of the forces as homogenous as possible from the longitudinal support to the spring chuck 7 which might easily jam in the cavity 6.

The head 9 of the pedicle screw 2 is preferably provided at its upper end with a hexagonal socket 23 to screw in the pedicle screw 2 into the bone by means of a hexagon screw driver.

In FIG. 3, a variant of the device according to the invention is represented by which the retainer head provides an upwardly open threadened through hole 13 which communicates with the channel 5 wherein a tension means 10 with hexagon socket 24 is screwable such that a longitudinal support 1 inserted into the channel 5 is axially and rotationally fixable.

In FIG. 4, another variant of the device according to the invention following FIG. 3 is represented where the channel 5 is open towards one side to accept the longitudinal support 1 from the side. Instead of the hexagon socket 24, the tension means 10 of FIG. 3 can also be provided with a transverse slot 22 and an internal thread 30 (as shown in FIG. 4). The transverse slot 22 and the internal thread 30 in this case serve to the acceptance of a manipulating device (not shown in the drawings).

In FIG. 5, a further variant of the device according to the invention is represented wherein the channel 5 is similarly open to one side as in the variant according to FIG. 4. However, the retainer head 3 provides at its upper section 14 an external thread 15 with a transverse slot 25 and an internal thread 30 around which the hollow cylindric sleeve 16 with the recesses 18 can be reverse drawn onto the longitudinal support 1. Via the nut 17 which provides an internal thread corresponding to the external thread 15 the sleeve 16 can be tensioned against the longitudinal support 1 inserted in the channel 5 so that the longitudinal support 1 is axially and rotationally fixed on the one side and on the other side presses on the insert 12 respectively via the opening 11 on the spring chuck 7.

By the further variant of the device according to the invention shown in FIG. 6, the retainer head 3 is slablike shaped; it contains apart from the cavity 6 tapering conically downwards with the central axis 4 the channel 5,—fully closed—and running transverse to the latter to the acceptance of the longitudinal support 1 with the longitudinal axis 32. The fixation of the spring chuck 7 happens via the tension means 10 which presses onto the washer 12. The washer 12 can in case of this embodiment be omitted without any problem so that the tension means presses directly on the spring chuck 7. Through the pressure on the spring chuck 7 it glides downwards within the conically tapering cavity 6 therewith contracting itself in diameter so that an inserted preferably spherical head of a pedicle screw is fastened.

In this embodiment the fixation of the longitudinal support separately happens via an additional locking screw 31 which can be screwed in from above in a bore hole communicating with the channel 5 until it reaches the longitudinal support.

The preferably spherical head 9 of the pedicle screw 2 can be provided instead of the hexagon socket with a device to attach an extension (not shown in the drawings) that enables a manipulation of the pedicle screw 2 through the tension means 10 (this needs a large, through opening). The connection between pedicle screw 2 and the extension is preferably reversible and stable in view to rotation, tension and pressure.

The variant of the device according to the invention shown in FIG. 7 demonstrates the application of a tension means 10 and a tensioning screw 36 in which a separate fixation of the longitudinal support 1 and the pedicle screw 2 is possible. The tensioning screw 36 is screwed into the retainer head and fastens only the spherical head 9 of the pedicle screw 2. Hence, the screw can be displaced along the longitudinal support with its spherical head fastened without varying the angle between longitudinal support 1 and pedicle screw 2. The tension means 10 for the fixation of the longitudinal support is inserted into a hole in tensioning screw 36. The acceptance of the longitudinal support 1 in the retainer head 3 can be realized as shown in FIG. 1 through a upwardly open channel 5.

The acceptance of the longitudinal support 1 is possible as well by a bore hole a shown in FIG. 3 or by a sidewardly placed open channel 5 according to FIG. 4. The acceptance of the longitudinal support 1 in the insert 12 is possible by a bore hole 43 according to FIG. 8. For the simplification of the mounting in case of upwardly open retainer head 3 according to FIG. 1, an insert 12 has an upwardly open channel 37 (as shown in FIG. 7). In contrast to the embodiment of FIGS. 8 and 9, however, the insert 12 is sufficiently open on top that the tension means 10 presses umimpeded directly on the longitudinal support 1. The foregoing catenation of the insert 12 on the longitudinal support 1 is not necessary. It is possible, too to provide the insert 12 with a sideward channel 5 according to FIG. 5. The mounting of the insert 12 is preferably done from the side of the spring chuck 7. A rim 39 at the insert 12 hinders the insert from sliding upwardly out of the retainer head 3. The sliding out towards below is hindered by the spring chuck 7. In case of use of a retainer head 3 which is upwardly open because of the channel 5 and of a tensioning screw 36 a safety sleeve 41 prevents the retainer head 3 from widening when the tensioning screw 36 is tightened. Instead of the tensioning screw 36, a tensioning nut 38 similarly as shown in FIG. 9 is possible.

In FIG. 8, a further variant of the device according to the invention is shown. Similarly to the variant shown in FIG. 7 a second tensioning screw 36 fixes the spherical head 9 via the insert 12 without jamming the longitudinal support. In contrast to the variant shown in FIG. 7, the tension means 10, which fixes the longitudinal support 1, is inserted in the insert 12, which, is further drawn up and provided with an internal thread 42. The insert 12 provides a closed upwardly open thread hole 42. The closed bottom of the insert 12 provides homogeneous pressures on the spring chuck 7. The acceptance of the longitudinal support 1 in the retainer head 3 may be realized by an upwardly open channel 5, (as shown in FIG. 1), a bore hole (as shown in FIG. 3), or by a sidewards placed open channel 5 (as shown in FIG. 4). As shown in FIG. 8, insert 12 has a bore hole 43 for receiving longitudinal support 1. The insert 12 must be catenated on the longitudinal support 1 before the longitudinal support 1 is inserted into the retainer head 3. An upwardly open channel 5 at the insert 12 as shown in FIG. 7 is possible too if the diameter of the longitudinal support 1 is approximately ⅗ of the core diameter of the internal thread 42. In case of use of a retainer head 3 which is upwardly open, because of the channel 5 and of a tension screw 36, a safety sleeve 41 prevents a widening of the retainer head 3 when the tensioning screw 36 is tightened. Instead of the tensioning screw 36, a tensioning nut 38 similar as shown in FIG. 9 is possible.

The variant of the device according to the invention shown in FIG. 9 is marked as shown in FIG. 8 through a drawn up insert 12 and a tension means 10 fixation of the longitudinal support 1 integrated therein. Whereas the spring chuck 7 is fixed via a tensioning nut 38. This tensioning nut 38 presses on the insert 12 and the spring chuck 7 whereby the spherical head 9 is fixed without jamming the longitudinal support 1. A second tension means 10 runs in the insert 12 and jams the longitudinal support 1. The fixations of the spherical head 9 and the longitudinal support 1 are so mechanically decoupled. The acceptance of the longitudinal support 1 may be realized by an upwardly open channel 5 as shown in FIG. 1. An acceptance of the longitudinal support 1 via a bore hole as shown in FIG. 3 or via a sidewardly placed open channel 5 according to FIG. 4 is possible as well. The acceptance of the longitudinal support 1 in the insert 12 is possible through a bore hole 43 according to FIG. 8. For the simplification of the mounting in case of an upwardly open retainer head 3 according to FIG. 1 an insert 12 provided with an upwardly open channel 37 according to FIG. 9 is insertable. The longitudinal support 1 then can be introduced from above into the insert 12. A foregoing catenation of the insert 12 on the longitudinal support 1 is not necessary. It is possible as well to provide the insert 12 with a sidewardly channel 5 according to FIG. 4. The mounting of the insert 12 preferably takes place from the side of the spring chuck 7. A rim 39 at the insert 12 hinders a sliding out of the insert 12 towards the top of the retainer head 3. The sliding out towards the bottom is hindered through the spring chuck 7.

What is claimed is:

1. A spinal fixation system comprising:
    a longitudinal member positionable along a spinal column;
    a fastener having a threaded end for engaging a vertebra; and
    a connector member for connecting the fastener and the longitudinal member, said connector member having top, bottom, and side surfaces, and comprising:
        a channel extending through the side surfaces for receiving the longitudinal member;
        a tapered opening extending through the bottom surface for receiving the fastener;
        a top opening extending through the top surface and operatively associated with the tapered opening;
        a fastener clamping element having a hollow truncated cone shape, top and bottom surfaces, and a plurality of slots, the element securing the fastener in the tapered opening at a surgeon selected angle relative to the connector member and longitudinal member; and
        a tension element insertable in the top opening,
    wherein insertion of the tension element in the top opening causes downward movement of the fastener clamping element in the tapered opening and thereby radial compression of the fastener clamping element to secure the fastener at the surgeon selected angle.

2. The spinal fixation system of claim 1 wherein the plurality of slots of the fastener clamping element includes first slots intersecting the top surface and second slots intersecting the bottom surface.

3. The spinal fixation system of claim 1 wherein the fastener clamping element has a half cone angle which is between about 3° and 8°.

4. The spinal fixation system of claim 1 wherein the tapered opening has a half cone angle which is between about 3° and 8°.

5. The spinal fixation system of claim 1 wherein the fastener clamping element is radially compressible in diameter between about 0.8 mm and 1.2 mm.

6. The spinal fixation system of claim 1 wherein the fastener clamping element radially expands in diameter between about 0.3 mm and 0.6 mm for receiving the fastener.

7. The spinal fixation system of claim 1 wherein the fastener clamping element has a substantially concavely shaped interior.

8. The spinal fixation system of claim 7 wherein the fastener has a substantially spherical head.

9. The spinal fixation system of claim 8 wherein the spherical head includes at least one of fins or grooves for securing the fastener in the fastener clamping element at the surgeon selected angle.

10. The spinal fixation system of claim 8 wherein the head of the fastener is made of a material having a hardness which is greater than that of the interior of the fastener clamping element.

11. The spinal fixation system of claim 10 wherein the head is made of a Ti—Al—Nb alloy and the fastener clamping element is made of titanium.

12. The spinal fixation system of claim 8 wherein the diameter of the spherical head is between about 6 mm and 10 mm.

13. The spinal fixation system of claim 1 wherein the channel is oriented transversely to the tapered opening so that insertion of the tension element in the top opening fixes the longitudinal member in the channel.

14. The spinal fixation system of claim 13 wherein the head is spaced between about 4 mm and 10 mm from the longitudinal member.

15. The spinal fixation system of claim 13 further comprising a hollow cylindrical insert positioned between the longitudinal member and the fastener clamping element, wherein insertion of the tension element in the top opening presses against the longitudinal member thereby pressing the insert against the fastener clamping element.

16. The spinal fixation system of claim 1 wherein the tension element has an exterior surface that includes threads and at least a portion of walls of the top opening are threaded for threadably receiving the tension element.

17. The spinal fixation system of claim 1 wherein the channel includes an opening to allow insertion of the longitudinal member in the channel.

18. The spinal fixation system of claim 17 wherein the tension element comprises a fastener tensioning screw for securing the fastener at the surgeon selected angle and having a through opening with a threaded wall; and a longitudinal member tensioning screw threadably received in the through opening for securing the longitudinal member in the channel.

19. The spinal fixation system of claim 1 wherein the tapered opening is laterally displaced from the channel.

20. The spinal fixation system of claim 19 further comprising a longitudinal member clamping element for securing the longitudinal member in the channel.

* * * * *